(12) United States Patent
Grey et al.

(10) Patent No.: US 7,696,367 B2
(45) Date of Patent: Apr. 13, 2010

(54) DIRECT EPOXIDATION PROCESS USING A MIXED CATALYST SYSTEM

(75) Inventors: Roger A. Grey, West Chester, PA (US); Steven M. Augustine, Ellicott City, MD (US)

(73) Assignee: Lyondell Chemical Technology, L.P., Houston, TX (US)

( * ) Notice: Subject to any disclaimer, the term of this patent is extended or adjusted under 35 U.S.C. 154(b) by 621 days.

(21) Appl. No.: 11/784,911

(22) Filed: Apr. 10, 2007

(65) Prior Publication Data

US 2008/0255379 A1    Oct. 16, 2008

(51) Int. Cl.
*C07D 301/06* (2006.01)
*C07D 301/12* (2006.01)
(52) U.S. Cl. ...................... 549/533; 549/531
(58) Field of Classification Search .................. 549/531, 549/533
See application file for complete search history.

(56) References Cited

U.S. PATENT DOCUMENTS

| 3,351,635 | A | 11/1967 | Kollar | 260/348.5 |
|---|---|---|---|---|
| 4,367,342 | A | 1/1983 | Wulff et al. | 549/529 |
| 4,410,501 | A | 10/1983 | Taramasso et al. | 423/326 |
| 4,666,692 | A | 5/1987 | Taramasso et al. | 423/326 |
| 4,833,260 | A | 5/1989 | Neri et al. | 549/531 |
| 4,859,785 | A | 8/1989 | Bellussi et al. | 549/531 |
| 4,937,216 | A | 6/1990 | Clerici et al. | 502/62 |
| 5,859,265 | A | 1/1999 | Müller et al. | 549/531 |
| 6,307,073 | B1 | 10/2001 | Jones | 549/532 |
| 6,498,259 | B1 | 12/2002 | Grey et al. | 549/533 |

FOREIGN PATENT DOCUMENTS

| BE | 1001038 A7 | 6/1989 |
|---|---|---|
| JP | 4-352771 | 12/1992 |
| WO | WO 98/00413 | 1/1998 |

OTHER PUBLICATIONS

Edwards, et al., *Journal of Catalysis* 236 (2005) 69-79.
Li et al., *Catalysis Communications* 8 (2007) 247-250.

*Primary Examiner*—Bernard Dentz
(74) *Attorney, Agent, or Firm*—Kevin M. Carroll

(57) ABSTRACT

The invention is a process for epoxidizing an olefin with hydrogen and oxygen in the presence of a catalyst mixture containing a titanium or vanadium zeolite and a supported catalyst comprising palladium, gold, and an inorganic oxide carrier. Prior to its use in the epoxidation process, the supported catalyst is calcined in the presence of oxygen at a temperature from 450 to 800° C. and reduced in the presence of hydrogen at a temperature greater than 20° C. The process results in significantly reduced alkane byproduct formed by the hydrogenation of olefin.

20 Claims, No Drawings

DIRECT EPOXIDATION PROCESS USING A MIXED CATALYST SYSTEM

FIELD OF THE INVENTION

This invention relates to an epoxidation process using a mixed catalyst system to produce epoxides from hydrogen, oxygen, and olefins.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide oxidizing agent, such as ethylbenzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst. Unfortunately, the silver catalyst has not proved useful in commercial epoxidation of higher olefins.

Besides oxygen and alkyl hydroperoxides, another oxidizing agent useful for the preparation of epoxides is hydrogen peroxide. U.S. Pat. Nos. 4,833,260, 4,859,785, and 4,937,216, for example, disclose the epoxidation of olefins with hydrogen peroxide in the presence of a titanium silicate catalyst.

Much current research is conducted in the direct epoxidation of olefins with oxygen and hydrogen. In this process, it is believed that oxygen and hydrogen react in situ to form an oxidizing agent. Many different catalysts have been proposed for use in the direct epoxidation of higher olefins. Typically, the catalyst comprises a noble metal that is supported on a titanosilicate. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form a hydrogen peroxide in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

Mixed catalyst systems for olefin epoxidation with hydrogen and oxygen have also been disclosed. For example, JP 4-352771 at Example 13 describes the use of a mixture of titanosilicate and Pd/C for propylene epoxidation. U.S. Pat. Nos. 6,498,259 and 6,307,073 also describe olefin epoxidation with hydrogen and oxygen in the presence of a catalyst mixture containing a titanium zeolite and a supported catalyst comprising a noble metal and a support. In addition, recent work has demonstrated the effectiveness of a Pd—Au supported catalysts for the synthesis of hydrogen peroxide from hydrogen and oxygen. See Journal of Catalysis, 236 (2005) 69-79 and Catalysis Communications, 8 (2007) 247-250.

One disadvantage of the described direct epoxidation catalysts is that they are prone to produce non-selective byproducts such as glycols or glycol ethers formed by the ring-opening of the epoxide product or alkane byproduct formed by the hydrogenation of olefin.

In sum, new processes for the direct epoxidation of olefins are needed. Particularly valuable processes would have good productivity and selectivity to epoxides, while reducing the likelihood of alkane byproduct formation by the hydrogenation of olefin.

SUMMARY OF THE INVENTION

The invention is an olefin epoxidation process that comprises reacting an olefin, hydrogen and oxygen in the presence of a titanium or vanadium zeolite and a supported catalyst. The supported catalyst comprises palladium, gold and an inorganic oxide carrier, that has been calcined in the presence of oxygen at a temperature from 450 to 800° C. and reduced in the presence of hydrogen at a temperature greater than 20° C. This process surprisingly gives significantly reduced alkane byproduct formed by the hydrogenation of olefin.

DETAILED DESCRIPTION OF THE INVENTION

The process of the invention employs a catalyst mixture that comprises (1) a titanium or vanadium zeolite and (2) a supported catalyst which comprises palladium, gold and an inorganic oxide carrier. Titanium or vanadium zeolites comprise the class of zeolitic substances wherein titanium or vanadium atoms are substituted for a portion of the silicon atoms in the lattice framework of a molecular sieve. Such substances, and their production, are well known in the art. See for example, U.S. Pat. Nos. 4,410,501 and 4,666,692.

Suitable titanium or vanadium zeolites are those crystalline materials having a porous molecular sieve structure with titanium or vanadium atoms substituted in the framework. The choice of titanium or vanadium zeolite employed will depend upon a number of factors, including the size and shape of the olefin to be epoxidized. For example, it is preferred to use a relatively small pore titanium or vanadium zeolite such as a titanium silicalite if the olefin is a lower aliphatic olefin such as ethylene, propylene, or 1-butene. Where the olefin is propylene, the use of a TS-1 titanium silicalite is especially advantageous. For a bulky olefin such as cyclohexene, a larger pore titanium or vanadium zeolite such as a zeolite having a structure isomorphous with zeolite beta may be preferred.

Particularly preferred titanium zeolites include the class of molecular sieves commonly referred to as titanium silicalites, particularly "TS-1" (having an MFI topology analogous to that of the ZSM-5 aluminosilicate zeolites), "TS-2" (having an MEL topology analogous to that of the ZSM-11 aluminosilicate zeolites), and "TS-3" (as described in Belgian Pat. No. 1,001,038). Titanium-containing molecular sieves having framework structures isomorphous to zeolite beta, mordenite, ZSM-48, ZSM-12, and MCM-41 are also suitable for use. The titanium zeolites preferably contain no elements other than titanium, silicon, and oxygen in the lattice framework, although minor amounts of boron, iron, aluminum, sodium, potassium, copper and the like may be present.

Preferred titanium zeolites will generally have a composition corresponding to the following empirical formula $xTiO_2$ $(1-x)SiO_2$ where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable.

The catalyst mixture employed in the process of the invention also comprises a supported catalyst. The supported catalyst comprises palladium, gold and an inorganic oxide carrier. The inorganic oxide carrier is preferably a porous material. Inorganic oxide carriers are well-known in the art. Preferred inorganic oxides include oxides of Group 2, 3, 4, 5, 6, 13, or 14 elements. Particularly preferred inorganic oxide carriers include silica, alumina, silica-aluminas, titania, zirconia, niobium oxides, tantalum oxides, molybdenum oxides, tungsten oxides, amorphous titania-silica, amorphous zirconia-silica, amorphous niobia-silica, and the like. The carrier may be a zeolite, but is not a titanium or vanadium zeolite. Particularly preferred inorganic oxide carriers include alumina, silica, silica-aluminas, titania, zirconia, and niobia. Titanium dioxide is most preferred.

Preferably, the inorganic oxide carrier has a surface area in the range of about 1 to about 700 m$^2$/g, most preferably from about 10 to about 500 m$^2$/g. Preferably, the pore volume of the carrier is in the range of about 0.1 to about 4.0 mL/g, more preferably from about 0.5 to about 3.5 mL/g, and most preferably from about 0.8 to about 3.0 mL/g. Preferably, the average particle size of the inorganic oxide carrier is in the range of about 0.1 μm to about 0.5 inch, more preferably from about 1 μm to about 0.25 inch, and most preferably from about 10 μm to about 1/16 inch. The preferred particle size is dependent upon the type of reactor that is used, for example, larger particle sizes are preferred for a fixed bed reaction. The average pore diameter is typically in the range of about 10 to about 1000 Å, preferably about 20 to about 500 Å, and most preferably about 50 to about 350 Å.

The supported catalyst also contains palladium and gold. Typically, the amount of palladium present in the supported catalyst will be in the range of from 0.01 to 20 weight percent, preferably 0.01 to 10 weight percent, and more preferably from 0.1 to 5 weight percent. The manner in which the palladium is incorporated into the supported catalyst is not considered to be particularly critical. For example, a palladium compound (for example, Pd tetraamine bromide) may be supported on the carrier by impregnation, adsorption, ion-exchange, precipitation, or the like.

There are no particular restrictions regarding the choice of palladium compound or complex used as the source of palladium in the supported catalyst. For example, suitable compounds include the nitrates, sulfates, halides (e.g., chlorides, bromides), carboxylates (e.g. acetate), and amine complexes of palladium.

The supported catalyst used in the process of the invention also contains gold. The typical amount of gold present in the supported catalyst will preferably be in the range of from about 0.01 to 10 weight percent, more preferably 0.01 to 5 weight percent, and most preferably from 0.1 to 2 weight percent. While the choice of gold compound used as the gold source in the supported catalyst is not critical, suitable compounds include gold halides (e.g., chlorides, bromides, iodides), nitrates, sulfates, carboxylates (e.g., acetate), cyanides, and sulfides and organoamine complexes of gold, as well as compounds containing a mixture of such ligands. The gold may be added to the carrier before, during, or after palladium addition. Any suitable method can be used for the incorporation of gold into the supported catalyst. As with palladium addition, the gold may be supported on the carrier by impregnation or the like. Incipient wetness and deposition-precipitation techniques may also be used to incorporate the gold.

Preferably, the supported catalyst of the invention also contains lead. The preferred amount of lead present in the supported catalyst will be in the range of from about 0.01 to 10 weight percent, more preferably 0.01 to 5 weight percent, and most preferably from 0.1 to 2 weight percent. Preferably, the weight ratio of palladium to lead in the catalyst is in the range of 1 to 100. While the choice of lead compound used as the lead source in the catalyst is not critical, suitable compounds include lead carboxylates (e.g., acetate), halides (e.g., chlorides, bromides, iodides), nitrates, cyanides, and sulfides. The lead may be added to the titanium or vanadium zeolite before, during, or after palladium addition, it is preferred to add the lead promoter at the same time that palladium is introduced. Any suitable method can be used for the incorporation of lead into the catalyst. As with palladium addition, the lead may be supported on the titanium or vanadium zeolite or the carrier by impregnation. Incipient wetness techniques may also be used to incorporate the lead.

After palladium and gold (and optionally, lead) incorporation, the supported catalyst is recovered. Suitable catalyst recovery methods include filtration and washing, rotary evaporation and the like. The supported catalyst is typically dried at a temperature greater than about 50° C. The drying temperature is preferably from about 50° C. to about 200° C. The supported catalyst may additionally comprise a binder or the like and may be molded, spray dried, shaped or extruded into any desired form prior to use in epoxidation.

After supported catalyst formation and prior to its use in the epoxidation process of the invention, the supported catalyst is thermally treated in the presence of oxygen and then reduced. The calcination may be conducted in pure oxygen atmosphere, but is preferably conducted in an oxygen-containing atmosphere, such as air or a mixture of oxygen and an inert gas such as nitrogen. The supported catalyst may also be pyrolyzed in the presence of an inert gas such as nitrogen prior to calcination in an oxygen-containing atmosphere. The calcination is conducted at a temperature in the range of from 450 to 800° C., preferably from about 550 to about 650° C.

Following the calcination, the supported catalyst is then reduced at a temperature of at least 20° C. in the presence of molecular hydrogen. The temperature range of from 50° C. to 500° C. is especially suitable. The molecular hydrogen may be combined with other gases such as nitrogen and the like. Preferably, the gas stream will comprise from about 1 to 30 volume percent hydrogen, more preferably from about 1 to 4 volume percent hydrogen. The reduction time is not critical, however typical heating times are from 0.1 to 48 hours.

The titanium or vanadium zeolite and the supported catalyst may be used in the epoxidation process as a mixture of powders or as a mixture of pellets. In addition, the titanium or vanadium zeolite and supported catalyst may also be pelletized or extruded together prior to use in epoxidation. If pelletized or extruded together, the catalyst mixture may additionally comprise a binder or the like and may be molded, spray dried, shaped or extruded into any desired form prior to use in epoxidation. The weight ratio of titanium or vanadium zeolite: supported catalyst is not particularly critical. However, a titanium or vanadium zeolite: supported catalyst ratio of 0.01-100 (grams of titanium or vanadium zeolite per gram of supported catalyst) is preferred, with a ratio of 1 to 20 more preferred, and a ratio of 5 to 15 most preferred.

The process of the invention comprises contacting an olefin, oxygen, and hydrogen in the presence of the catalyst mixture. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$-$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

Oxygen and hydrogen are also required for the epoxidation process. Although any sources of oxygen and hydrogen are suitable, molecular oxygen and molecular hydrogen are preferred.

Epoxidation according to the invention is carried out at a temperature effective to achieve the desired olefin epoxidation, preferably at temperatures in the range of 0-250° C., more preferably, 20-100° C. The molar ratio of hydrogen to oxygen can usually be varied in the range of $H_2:O_2=1:10$ to 5:1 and is especially favorable at 1:5 to 2:1. The molar ratio of oxygen to olefin is usually 2:1 to 1:20, and preferably 1:1 to 1:10. A carrier gas may also be used in the epoxidation process. As the carrier gas, any desired inert gas can be used. The molar ratio of olefin to carrier gas is then usually in the range of 100:1 to 1:10 and especially 20:1 to 1:10.

As the inert gas carrier, noble gases such as helium, neon, and argon are suitable in addition to nitrogen and carbon dioxide. Saturated hydrocarbons with 1-8, especially 1-6, and preferably with 1-4 carbon atoms, e.g., methane, ethane, propane, and n-butane, are also suitable. Nitrogen and saturated $C_1$-$C_4$ hydrocarbons are the preferred inert carrier gases. Mixtures of the listed inert carrier gases can also be used.

Specifically in the epoxidation of propylene, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

The amount of catalyst used may be determined on the basis of the molar ratio of the titanium contained in the titanium zeolite to the olefin that is supplied per unit time. Typically, sufficient catalyst is present to provide a titanium/olefin per hour molar feed ratio of from 0.0001 to 0.1.

Depending on the olefin to be reacted, the epoxidation according to the invention can be carried out in the liquid phase, the gas phase, or in the supercritical phase. When a liquid reaction medium is used, the catalyst is preferably in the form of a suspension or fixed-bed. The process may be performed using a continuous flow, semi-batch or batch mode of operation.

If epoxidation is carried out in the liquid (or supercritical or subcritical) phase, it is advantageous to work at a pressure of 1-100 bars and in the presence of one or more solvents. Suitable solvents include any chemical that is a liquid under reaction conditions, including, but not limited to, oxygenated hydrocarbons such as alcohols, ethers, esters, and ketones, aromatic and aliphatic hydrocarbons such as toluene and hexane, nitriles such as acetonitrile, liquid $CO_2$ (in the supercritical or subcritical state), and water. Preferable solvents include water, liquid $CO_2$, and oxygenated hydrocarbons such as alcohols, ethers, esters, ketones, and the like. Preferred oxygenated solvents include lower aliphatic $C_1$-$C_4$ alcohols such as methanol, ethanol, isopropanol, and tert-butanol, or mixtures thereof, and water. Fluorinated alcohols can be used. It is particularly preferable to use mixtures of the cited alcohols with water.

If epoxidation is carried out in the liquid (or supercritical) phase, it is advantageous to use a buffer. The buffer will typically be added to the solvent to form a buffer solution. The buffer solution is employed in the reaction to inhibit the formation of glycols or glycol ethers during epoxidation. Buffers are well known in the art.

Buffers useful in this invention include any suitable salts of oxyacids, the nature and proportions of which in the mixture, are such that the pH of their solutions may range from 3 to 10, preferably from 4 to 9 and more preferably from 5 to 8. Suitable salts of oxyacids contain an anion and cation. The anion portion of the salt may include anions such as phosphate, sulfate, carbonate, bicarbonate, carboxylates (e.g., acetate, phthalate, and the like), citrate, borate, hydroxide, silicate, aluminosilicate, or the like. The cation portion of the salt may include cations such as ammonium, alkylammoniums (e.g., tetraalkylammoniums, pyridiniums, and the like), alkali metals, alkaline earth metals, or the like. Cation examples include $NH_4$, $NBu_4$, $NMe_4$, Li, Na, K, Cs, Mg, and Ca cations. More preferred buffers include alkali metal phosphate and ammonium phosphate buffers. Buffers may preferably contain a combination of more than one suitable salt. Typically, the concentration of buffer in the solvent is from about 0.0001 M to about 1 M, preferably from about 0.001 M to about 0.3 M. The buffer useful in this invention may also include the addition of ammonia gas to the reaction system.

The following examples merely illustrate the invention. Those skilled in the art will recognize many variations that are within the spirit of the invention and scope of the claims.

EXAMPLE 1

Preparation of Pd—Au (Pb) Catalysts

Catalyst 1A (Pd—Au/$TiO_2$): Aqueous sodium tetrachloro aurate (16.54 g, 19.95 wt. % Au) and aqueous disodium tetrachloro palladate (27.86 g, 19.74 wt. % Pd) is added with swirling to 1.2 L of deionized water in a roundbottom flask. Sodium bicarbonate powder (12.5 g) is then added to this solution followed by spray dried $TiO_2$ (500 g, 35 micron average size, air calcined at 700° C., 43 $m^2/g$). The pH of the slurry is adjusted to 7.3 by adding solid portions of sodium bicarbonate (approximately 100 g total) and the reaction slurry is agitated by rotation of the flask at 25 rpm at a 45 degree angle for 18 hours at 23° C. The solids are filtered, washed once with 1.2 L of deionized water, and then calcined in air in a muffle furnace by heating at 10° C./min to 110° C. for 4 hours and then heating at 2° C./min to 300° C. for 4 hours. The calcined solids are then washed eight more times with 1.2 L portions of deionized water and dried in vacuum (2 torr) at 50° C. for 4 hours. The solids are then calcined in air in a muffle furnace by heating at 10° C./min to 110° C. for 4 hours and then heating at 2° C./min to the calcination temperature shown in Table 1 for 4 hours. The solids are then transferred to a quartz tube and treated with a 4 vol. % hydrogen/nitrogen stream (100 cc/hr) at the reduction temperature shown in Table 1 (typically 100° C.) for 1 hour, followed by nitrogen as the catalyst cooled to room temperature. The final solids contain 1 wt. % Pd, 0.6 wt. % Au, 58 wt. % Ti, and less than 20 ppm chloride.

Catalyst 1B (Pd—Au—Pb/$TiO_2$): Aqueous sodium tetrachloro aurate (16.62 g, 19.95 wt. % Au), aqueous disodium tetrachloro palladate (27.86 g, 19.74 wt. % Pd), and powder lead nitrate (5.2 g) is added with swirling to 1.2 L of deionized water in a roundbottom flask. Spray dried $TiO_2$ (500 g, 35 micron average size, air calcined at 700° C., 43 $m^2/g$) is then added to this solution and the pH of the slurry is adjusted to 5.96 by adding solid portions of sodium bicarbonate (approximately 16 g total). The reaction slurry is agitated by rotation of the flask at 25 rpm at a 45 degree angle for 6 hours at 40° C. The solids are filtered, washed once with 1.2 L of deionized water, and then calcined in air in a muffle furnace by heating at 10° C./min to 110° C. for 4 hours and then heating at 2° C./min to 300° C. for 4 hours. The calcined solids are then washed eight more times with 1.2 L portions of deionized water and dried in vacuum (2 torr) at 50° C. for 4 hours. The solids are then calcined in air in a muffle furnace by heating at 10° C./min to 110° C. for 4 hours and then heating at 2° C./min to the calcination temperature shown in Table 1 for 4 hours. The solids are then transferred to a quartz tube and treated with a 4 vol. % hydrogen/nitrogen stream (100 cc/hr) at 100° C. for 1 hour, followed by nitrogen as the catalyst cooled to room temperature. The final solids contain 0.9 wt. % Pd, 0.6 wt. % Au, 0.5 wt. % Pb, 58 wt. % Ti, and less than 20 ppm chloride.

Catalyst 1C (Pd—Au/Al$_2$O$_3$): A Pd—Au on alumina powder (containing 0.9 wt. % Pd and 0.53 wt. % Au, surface area=4 m$^2$/g) is calcined in air in a muffle furnace by heating at 10° C./min to 110° C. for 4 hours and then heating at 2° C./min to the calcination temperature shown in Table 1 for 4 hours. The solids are then transferred to a quartz tube and treated with a 4 vol. % hydrogen/nitrogen stream (100 cc/hr) at the reduction temperature shown in Table 1 (typically 100° C.) for 1 hour, followed by nitrogen as the catalyst cooled to room temperature.

COMPARATIVE EXAMPLE 2

Preparation of Pd/TiO$_2$ Catalyst

Aqueous disodium tetrachloro palladate (27.86 g, 19.74 wt. % Pd) is added with swirling to 1.2 L of deionized water in a roundbottom flask, followed by spray dried TiO$_2$ (500 g, 35 micron average size, air calcined at 700° C., 43 m$^2$/g). The pH of the slurry is adjusted to 6.0 by adding solid portions of sodium bicarbonate (approximately 15.5 g total) and the reaction slurry is agitated by rotation of the flask at 25 rpm at a 45 degree angle for 4 hours at 40° C. The solids are filtered, washed once with 1.2 L of deionized water, and then calcined in air in a muffle furnace by heating at 10° C./min to 110° C. for 4 hours and then heating at 2° C./min to 300° C. for 4 hours. The calcined solids are then washed eight more times with 1.2 L portions of deionized water and dried in vacuum (2 torr) at 50° C. for 4 hours. The solids are then calcined in air in a muffle furnace by heating at 10° C./min to 110° C. for 4 hours and then heating at 2° C./min to the calcination temperature shown in Table 2 for 4 hours. The solids are then transferred to a quartz tube and treated with a 4 vol. % hydrogen/nitrogen stream (100 cc/hr) at 100° C. for 1 hour, followed by nitrogen as the catalyst cooled to room temperature. The final solids contain 0.9 wt. % Pd.

COMPARATIVE EXAMPLE 3

Preparation of Pd/TS-1 Catalyst

Spray dried TS1 (15.778 pounds; 20 wt. % silica binder, 2.1 wt. % Ti, calcined at 550° C.) is added to deionized water (17.89 L) in a 50 liter mixing tank and stirred by an agitator at 500 rpm. The pH of the slurry is adjusted up to 7.0 using 3% aqueous ammonium hydroxide, then tetraammine palladium nitrate aqueous solution (0.166 pounds Pd, diluted to 1 liter) is added over a one-minute period through a subsurface injection, with agitation. The pH of the slurry is maintained at 7.0 during the palladium addition by adding the 3% ammonium hydroxide solution. After palladium addition, the pH is adjusted up to 7.5 with ammonium hydroxide and the slurry is agitated at 30° C. for 60 minutes while maintaining the pH at 7.4. The slurry is filtered and washed (three times with 17 L of deionized water) and the solids are dried in vacuum at 50° C. until a constant weight is obtained. The solids are then calcined in air in a muffle furnace by heating at 10° C./min to 110° C. for 4 hours and then heating at 2° C./min to the calcination temperature shown in Table 2 for 4 hours. The solids are then transferred to a quartz tube and treated with a 4 vol. % hydrogen/nitrogen stream (100 cc/hr) at 100° C. for 1 hour, followed by nitrogen as the catalyst cooled to room temperature. Comparative Catalyst 3 contains 0.1 wt. % Pd.

EXAMPLE 4

Epoxidation Reactions

A 300 cc stainless steel reactor is charged with a catalyst mixture of the supported Pd catalyst (0.07 g) and TS1 powder (0.63 g, 2 wt. % Ti) [or just 0.7 g of Pd/TS-1 from Comparative Example 3], a buffer (13 g, 0.1 M aqueous ammonium phosphate, pH=6), and methanol (100 g). The reactor is then charged to 300 psig of a feed consisting of 2% hydrogen, 4% oxygen, 5% propylene, 0.5% methane and the balance nitrogen (volume %). The pressure in the reactor is maintained at 300 psig via a back pressure regulator with the feed gases passed continuously through the reactor at 1600 cc/min (measured at 23° C. and one atmosphere pressure). In order to maintain a constant solvent level in the reactor during the run, the oxygen, nitrogen and propylene feeds are passed through a two-liter stainless steel vessel (saturator) preceding the reactor containing 1.5 liters of methanol. The reactor is stirred at 1500 rpm. The reaction mixture is heated to 60° C. and the gaseous effluent is analyzed by an online GC every hour and the liquid analyzed by offline GC at the end of the 18 hour run. Propylene oxide and equivalents (POE), which include propylene oxide ("PO"), propylene glycol ("PG"), and propylene glycol methyl ethers (PMs), are produced during the reaction, in addition to propane formed by the hydrogenation of propylene. The results of the GC analyses are used to calculate the selectivities shown in Tables 1 and 2.

The epoxidation results (see Tables 1 and 2) demonstrate that a mixed catalyst system (TS-1+Pd—Au(Pb)/inorganic oxide) shows a significant reduction in propane make when calcined at temperatures in the range of 450-800° C.

TABLE 1

Temperature Difference in Propane Selectivity

| Catalyst | Catalyst Productivity[1] | Calcination Temp (° C.) | Reduction Temp (° C.) | Propylene Selectivity (%)[2] |
|---|---|---|---|---|
| 1A* | 0.7 | 300 | 100 | 68 |
| 1A | 0.37 | 550 | 100 | 80 |
| 1A | 0.41 | 550 | 400 | 79 |
| 1A | 0.36 | 600 | 100 | 84 |
| 1A | 0.36 | 650 | 100 | 84 |
| 1A | 0.35 | 700 | 100 | 82 |
| 1A | 0.34 | 750 | 100 | 77 |
| 1A | 0.3 | 800 | 100 | 67 |
| 1B* | 0.57 | 300 | 100 | 69 |
| 1B* | 0.47 | 400 | 100 | 78 |
| 1B | 0.49 | 450 | 100 | 82 |
| 1B | 0.5 | 500 | 100 | 83 |
| 1B | 0.5 | 600 | 100 | 92 |
| 1B | 0.48 | 625 | 100 | 89 |
| 1B | 0.5 | 650 | 100 | 90 |
| 1B | 0.43 | 700 | 100 | 88 |
| 1B | 0.32 | 750 | 100 | 88 |
| 1C* | 0.54 | 300 | 100 | 50 |
| 1C* | 0.49 | 350 | 100 | 58 |
| 1C | 0.44 | 450 | 100 | 72 |
| 1C | 0.43 | 550 | 100 | 75 |
| 1C | 0.33 | 600 | 100 | 74 |
| 1C | 0.35 | 600 | 400 | 69 |

[1] Productivity = grams POE produced/gram of catalyst per hour.
[2] Propylene Selectivity = 100 − (moles propane/moles POE + moles propane) * 100.
*Comparative Example

TABLE 2

Catalyst Difference in Propane Selectivity

| Catalyst | Catalyst Productivity[1] | Calcination/ Reduction Temps (° C.) | Propylene Selectivity (%)[2] | Difference in Propylene Sel. (600 vs 300) |
|---|---|---|---|---|
| 1A* | 0.7 | 300/100 | 68 | 16 |
| 1A | 0.36 | 600/100 | 84 | |
| 1B* | 0.57 | 300/100 | 69 | 23 |
| 1B | 0.5 | 600/100 | 92 | |
| 1C* | 0.54 | 300/100 | 50 | 24 |
| 1C | 0.33 | 600/100 | 74 | |
| 2* | 0.36 | 300/100 | 74 | 7 |
| 2* | 0.44 | 600/100 | 81 | |
| 3* | 0.37 | 300/100 | 68 | 12 |
| 3* | 0.27 | 600/100 | 80 | |

[1]Productivity = grams POE produced/gram of catalyst per hour.
[2]Propylene Selectivity = 100 − (moles propane/moles POE + moles propane) * 100.
*Comparative Example

We claim:

1. A process for producing an epoxide comprising reacting an olefin, hydrogen and oxygen in the presence of a titanium or vanadium zeolite and a supported catalyst comprising palladium, gold, and an inorganic oxide carrier, wherein prior to its use in the process the supported catalyst is calcined in the presence of oxygen at a temperature within the range of 450 to 800° C. and reduced in the presence of hydrogen at a temperature greater than 20° C.

2. The process of claim 1 wherein the supported catalyst is calcined at a temperature within the range of 550 to 650° C.

3. The process of claim 1 wherein the titanium zeolite is a titanium silicalite.

4. The process of claim 1 wherein the supported catalyst contains 0.01 to 10 weight percent palladium and 0.01 to 5 weight percent gold.

5. The process of claim 1 wherein the supported catalyst further comprises lead.

6. The process of claim 1 wherein the inorganic oxide carrier is selected from the group consisting of titanias, zirconias, niobias, silicas, aluminas, silica-aluminas, tantalum oxides, molybdenum oxides, tungsten oxides, titania-silicas, zirconia-silicas, niobia-silicas, and mixtures thereof.

7. The process of claim 1 wherein the inorganic oxide carrier is titanium dioxide.

8. The process of claim 1 wherein the reaction is performed in the presence of a solvent.

9. The process of claim 8 wherein the solvent is an oxygenated solvent.

10. The process of claim 9 wherein the oxygenated solvent is selected from the group consisting of alcohols, ethers, esters, ketones, water, and mixtures thereof.

11. The process of claim 1 wherein the olefin is a $C_2$-$C_6$ olefin.

12. The process of claim 11 wherein the olefin is propylene.

13. The process of claim 8 wherein the reaction is performed in the presence of a buffer.

14. A process for producing propylene oxide comprising reacting propylene, hydrogen and oxygen in an oxygenated solvent in the presence of a titanium silicalite and a supported catalyst comprising palladium, gold, and titanium dioxide, wherein prior to its use in the process the supported catalyst is calcined in the presence of oxygen at a temperature within the range of 450 to 800° C. and reduced in the presence of hydrogen at a temperature greater than 20° C.

15. The process of claim 14 wherein the supported catalyst is calcined at a temperature within the range of 550 to 650° C.

16. The process of claim 14 wherein the titanium silicalite is TS-1.

17. The process of claim 14 wherein the supported catalyst contains 0.01 to 10 weight percent palladium and 0.01 to 5 weight percent gold.

18. The process of claim 14 wherein the supported catalyst further comprises lead.

19. The process of claim 14 wherein the oxygenated solvent is selected from the group consisting of alcohols, ethers, esters, ketones, water, and mixtures thereof.

20. The process of claim 14 wherein the reaction is performed in the presence of a buffer.

* * * * *